US008377951B2

(12) United States Patent
Wilson

(10) Patent No.: US 8,377,951 B2
(45) Date of Patent: Feb. 19, 2013

(54) TRANSDERMAL ADMINISTRATION OF PHYCOTOXINS

(75) Inventor: Nestor Antonio Lagos Wilson, Santiago (CL)

(73) Assignee: Phytotox Limited (BM)

( * ) Notice: Subject to any disclaimer, the term of this patent is extended or adjusted under 35 U.S.C. 154(b) by 927 days.

(21) Appl. No.: 11/568,751

(22) PCT Filed: May 6, 2005

(86) PCT No.: PCT/US2005/015819

§ 371 (c)(1), (2), (4) Date: Nov. 6, 2006

(87) PCT Pub. No.: WO2005/110418

PCT Pub. Date: Nov. 24, 2005

(65) Prior Publication Data

US 2008/0045553 A1 Feb. 21, 2008

Related U.S. Application Data

(60) Provisional application No. 60/569,112, filed on May 7, 2004.

(51) Int. Cl.
*A61K 31/505* (2006.01)

(52) U.S. Cl. ........................................................ 514/267

(58) Field of Classification Search ................... 514/267
See application file for complete search history.

(56) References Cited

U.S. PATENT DOCUMENTS

| | | | | |
|---|---|---|---|---|
| 3,957,966 | A | 5/1976 | Valan | |
| 4,001,413 | A | 1/1977 | Adams et al. | |
| 4,022,899 | A | 5/1977 | Adams et al. | |
| 4,029,794 | A | 6/1977 | Adams et al. | |
| 4,537,776 | A | 8/1985 | Cooper | |
| 5,183,462 | A | 2/1993 | Borodic | |
| 5,298,019 | A | 3/1994 | Borodic | |
| 5,437,291 | A | 8/1995 | Pasricha et al. | |
| 5,504,117 | A | 4/1996 | Gorfine | |
| 5,562,907 | A | 10/1996 | Arnon | |
| 5,674,205 | A | 10/1997 | Pasricha et al. | |
| 5,714,468 | A | 2/1998 | Binder | |
| 5,721,215 | A | 2/1998 | Aoki et al. | |
| 5,837,265 | A | 11/1998 | Montal et al. | |
| 5,908,746 | A | 6/1999 | Suzuki et al. | |
| 6,030,974 | A | 2/2000 | Schwartz et al. | |
| 6,117,877 | A | 9/2000 | Fogel | |
| 6,143,306 | A | 11/2000 | Donovan | |
| 6,187,756 | B1 | 2/2001 | Lee et al. | |
| 6,261,572 | B1 | 7/2001 | Donovan | |
| 6,299,893 | B1 | 10/2001 | Schwartz et al. | |
| 6,306,423 | B1 | 10/2001 | Donovan et al. | |
| 6,326,020 | B1 | 12/2001 | Kohane et al. | |
| 6,358,926 | B2 | 3/2002 | Donovan | |
| 6,407,088 | B1 | 6/2002 | Dong et al. | |
| 6,416,765 | B1 | 7/2002 | Donovan | |
| 6,432,986 | B2 | 8/2002 | Levin | |
| 6,447,787 | B1 | 9/2002 | Gassner et al. | |
| 6,552,191 | B1 | 4/2003 | Zhou et al. | |
| 6,559,154 | B2 | 5/2003 | Kang et al. | |
| 6,599,906 | B1 | 7/2003 | Ku et al. | |
| 6,780,866 | B2 | 8/2004 | Ku et al. | |
| 2001/0046962 | A1 | 11/2001 | Graham | |
| 2001/0053369 | A1 | 12/2001 | Donovan | |
| 2001/0053370 | A1 | 12/2001 | Donovan | |
| 2002/0025327 | A1 | 2/2002 | Schmidt | |
| 2002/0086036 | A1 | 7/2002 | Walker | |
| 2002/0142010 | A1 | 10/2002 | Graham | |
| 2002/0161013 | A1 | 10/2002 | Liu et al. | |
| 2002/0176872 | A1 | 11/2002 | Aoki et al. | |
| 2002/0192240 | A1 | 12/2002 | Brooks et al. | |
| 2002/0198226 | A1 | 12/2002 | Ku et al. | |
| 2003/0036502 | A1 | 2/2003 | Gassner et al. | |
| 2003/0100574 | A1 | 5/2003 | Wilson | |
| 2003/0170296 | A1* | 9/2003 | Sintov et al. | 424/449 |
| 2004/0009180 | A1 | 1/2004 | Donovan | |
| 2004/0018213 | A1 | 1/2004 | Aoki et al. | |
| 2004/0028706 | A1 | 2/2004 | Aoki et al. | |

(Continued)

FOREIGN PATENT DOCUMENTS

| | | |
|---|---|---|
| CN | 1192903 | 9/1998 |
| CN | 1363275 | 8/2002 |

(Continued)

OTHER PUBLICATIONS

Barry, European Journal of Pharmaceutical Sciences, 2001;14(2):101-114.*

(Continued)

*Primary Examiner* — San-Ming Hui

(74) *Attorney, Agent, or Firm* — Arnall Golden Gregory LLP; Kimberly T. Bond; Clark G. Sullivan

(57) ABSTRACT

Pharmaceutical compositions for interfering with neuronal transmission comprising an effective amount of at least one tricyclic 3,4-propinoperhydropurine are disclosed. Preparations for facial rejuvenation are provided that comprise an effective amount of the composition of the invention and a facial cream. Methods of interfering with neuronal transmission comprising topical application of an effective amount of the pharmaceutical compositions of the invention are provided. In another aspect of the invention, effective amounts of the pharmaceutical compositions and a transdermal therapeutic system are provided for transdermal administration of at least one tricyclic 3,4-propinoperhydropurine. The pharmaceutical composition contains at least one at least one tricyclic 3,4-propinoperhydropurine, and may be formulated for transdermal drug delivery. The transdermal drug delivery system may be a laminated composite comprising a backing layer, a drug reservoir, and a means for affixing the composite to the skin.

26 Claims, No Drawings

U.S. PATENT DOCUMENTS

2005/0202093 A1 9/2005 Kohane et al.
2006/0122200 A1 6/2006 Wilson
2007/0280970 A1 12/2007 Wilson
2008/0021051 A1 1/2008 Wilson

FOREIGN PATENT DOCUMENTS

WO 9843619 10/1998
WO 9851290 11/1998
WO 0024419 A1 5/2000
WO 0222129 A1 3/2002
WO 03101483 A1 12/2003

OTHER PUBLICATIONS

Wheeler, Anthony H., "Therapeutic Uses of Botulinum Toxin", American Family Physician, vol. 55, No. 2, pp. 541-545, Feb. 1997.
Abedrapo et al., Dis. Colon Rectum, vol. 47, No. 4, Apr. 2004, p. 598.
Munchau, et al., "Uses of Botulinum Toxin Injection in Medicine Today", BMJ, vol. 320, pp. 161-165, Jan. 2000.
Bower, et al., "Nonprotein Neurotoxins", Clinical Toxicology, vol. 18, No. 7, pp. 813-863, 1981.
Compagnon, D. et al., "Accumulation of Paralytic Shellfish Poisoning Toxins in the Bivalve Aulacomya Ater and Two Carnivorous Gastropods Concholepas Concholepas and *Argobuccinum ranelliformes* during an *Alexandrium catenella* Bloom in Southern Chile," Journal of Shellfish Research, 1998, 67-73, vol. 17, No. 1.
Lagos, N. "Microalgal Blooms: A global issue with negative impact in Chile," Biol. Res., 1998, 375-386, vol. 31.
Andrinolo, D. et al. "Paralytic shellfish toxins in mussels and *Alexandrium tamarense* at Valdes Peninsula, Chubut, Patagonia, Argentina: kinetics of a natural depuration," Journal of Shellfish Research, 1999, 203-209, vol. 18, No. 1.
Andrinolo, D., Michea, L.F., Lagos, N., "Toxic effects, pharmacokinetics and clearance of saxitoxin, a component of paralytic shellfish poison (PSP), in cats," Toxicon, 1999, 447-464, vol. 37.
Lagos, N.W. and Andrinolo, D., "Paralytic shellfish poisoning (PSP): Toxicology and kinetics," Seafood and Freshwater Toxins, 2000, 203-215, vol. 10.
Lagos, N. et al., "Toxinas Paralizantes en microalgas. Un ejemplo de biodiversidad," Sustentabilidad de la Bioversidad, Universidad de Concepción, Chile, 2001, 253-264.
Lagos, N., "Principales Toxinas de origen Fitoplanctónico: Identificación y cuantificación mediante Cromatografia Líquida de Alta Resolución (HPLC)," Floraciones Algales Nocivas en el Cono sur Americano, Instituto Español de Oceanografia, 2002, 57-76.
Andrinolo, D. et al., "Toxicokinetics and toxicodynamics of gonyautoxins alter an oral toxin dose in cats," Toxicon, 2001, 699-709, vol. 40.
Andrinolo, D. et al., "Transport of the organic cations gonyautoxin 2/3 epimers, a paralytic shellfish poison toxin, through the human and rat intestinal epitheliums," Toxicon, 2002, 1389-1397, vol. 40.
Lagos, N.,"The first evidence of paralytic shellfish toxins in the freshwater cyanobacterium *Cylindrospermopsis raciborskii,* isolated from Brazil," Toxicon, 1999, 1359-1373, vol. 37.
Pereira, P. et al., "Paralytic shellfish toxins in the freshwater cyanobacterium *Aphanizomenon flos*-aquae, isolated from Montargil reservoir, Portugal," Toxicon, 2000, 1689-1702, vol. 38.
Rivas, M. et al., "Biochemical characterization and inhibitory effects of dinophysistoxin-1, okadaic acid and microcystine 1-r on protein phosphatase 2a purified from the mussel *Mytilus chilensis,*" Biol. Res. 2000, 197-206, vol. 33.
Uribe, J.C. et al., "First Report of Diarrhetic Shellfish Toxins in Magellanic Fjords, Southern Chile," Journal of Shellfish Research, 2001, 69-74, vol. 20, No. 1.
Borodic, G.E. and Pearce, L.B., "New Concepts in Botulinum Toxin Therapy," Drug Safety, 1994, 145-152, vol. 11, No. 3.
Carruthers, A., "Update on Botulinum Toxin," Skin Therapy Letter, 1999, vol. 4, No. 5.
Carruthers, J. and Carruthers, A., "Botulinum Toxin (Botox) Chemodenervation for Facial Rejuvenation," Facial Rejuvenation: Nonsurgical Modalities, 2001, 197-204, vol. 9, No. 2.
Carruthers, A., Kiene, K., and Carruthers, J., "Botulinum A exotoxin use in clinical dermatology," Journal of the American Academy of Dermatology, 1996, 788-797, vol. 34, No. 5, Part 1.
Hall, S. et al., "The Saxitoxins, Sources, Chemistry, and Pharmacology," Marine Toxins: Origin, Structure and Molecular Pharmacology, Chapter 3, 1990, 29-65.
Jankovic, J., and Brin, M.F., "Therapeutic Uses of Botulinum Toxin," New England Journal of Medicine, 1991, 1186-1194, vol. 324, No. 17.
Kao, C.Y., "Tetrodotoxin, Saxitoxin and Their Significance in the Study of Excitation Phenomena," Pharmacological Reviews, 1966, 997-1049, vol. 18, No. 2.
Long, R.R , Sargent, J.C., and Hammer, K., Paralytic shellfish poisoning: A case report and serial electrophysiologic observations, Neurology, 1990, 1310-1312, vol. 40.
Strichartz, G., "Structural Determinants of the Affinity of Saxitoxin for Neuronal Sodium Channels," J. Gen. Physiol., 1984, 281-305, vol. 84.
Choudhary, G. et al., "Energetic Localization of Saxitoxin in Its Channel Binding Site," Biophysical Journal, 2002, 912-919, vol. 83, No. 2.
Garrido, R. et al., "The Gonyautoxin 2/3 Epimers Reduces Anal Tone When Injected in the Anal Sphincter of Healthy Adults," Biological Research, 2004, 395-403, vol. 37.
Ikawa, M. et al., "Toxin Profiles of the Blue-Green Alga *Aphanizomenon flos-aque,*" Toxic Dinoflagellates, 1985, 299-304.
Jellett, J.F. et al., "Toxicological Evaluation of Saxitoxin, Neosaxitoxin, Gonyautoxin II, Gonyautoxin II plus III and Decarbamoylsaxitoxin with the Mouse Neuroblastoma Cell Bioassay," Toxicology in Vitro, 1995, 57-65, vol. 9, Issue 1.
Cohen, H. and Law-Yone, B., "Blowfish Toxin: A New Approach to Pain Management," Texas Pain Society, Printed from www.texaspain.org on Oct. 29, 2003.
Lagos, N. et al., "Paralytic Shellfish Poison: Toxins That Can Kill and Heal," Proceedings of the CB Medical Treatment Symposium: An Exploration of Present Capabilities and Future Requirements, 2004, 197-202.
Garcia, C. et al., "Human Intoxication with Paralytic Shellfish Poison: Clinical Parameters and Toxin Analysis in Plasma and Urine," Biological Research, 2005, 197-205, vol. 38.
Garcia, C. et al., "Paralytic Shellfish Poisoning: Post-Mortem Analysis of Tissue and Body Fluid Samples from Human Victims in the Patagonia Fjords," Toxicon, 2004, 149-158, vol. 43.
Lagos, N., "Paralytic Shellfish Poisoning Phycotoxins: Occurrence in South America," Comments on Toxicology, 2003, 175-193, vol. 9.
Garrido, Rogelio et al., "The Use of Gonyautoxin in the Treatment of Acute and Chronic Anal Fissures: A New Therapeutic Approach," Presented at International Council of Coloproctology, American Society of Colon and Rectal Surgeons, Dallas, TX, 2004.
Mitragotri, Samir, "Synergistic Effect of Enhancers for Transdermal Drug Delivery," Pharmaceutical Research, 2000, pp. 1354-1359, vol. 17, No. 11.
Matchet, L. and Boucaud, A., "Phonophoresis: Efficiency, Mechanisms and Skin Tolerance," International Journal of Pharmaceutics, 2002, pp. 1-15, vol. 243.
Tosti, A. et al., "Prevalence and Sources of Sensitization to Emulsifiers: A Clinical Study," Contact Dermatitis, 1990, pp. 68-72, vol. 23, No. 2. (Abstract only).
Supplementary European Search Report of European Patent Application No. 05743508, Apr. 18, 2008.
Supplementary European Search Report of European Patent Application No. 05746905, Apr. 17, 2008.
Supplementary European Search Report of European Patent Application No. 06752321, May 9, 2008.
Supplementary European Search Report of European Patent Application No. 05747904, Apr. 18, 2008.
Abedrapo, Mario A., et al., "A Mew Therapeutical Approach for Anal Fissure: Gonyautoxins", Gastroenterology, Apr. 2004, vol. 126, No. 4, Suppl. 2, p. A86, XP002477199 (Abstract Only).
Maria, Giorgio, MD, Cassetta, Emanuele, MD, Gui, Daniele, MD, Brisinda, MD, Bentivoglio, Anna Rita, MD and Albanese, Alberto, MD "A Comparison of Botulinum Toxin and Saline for the Treatment of Chronic Anal Fissure" The New England Journal of Medicine, Jan. 1998, pp. 217-220, vol. 338, No. 4.
Ho, Philip T., MD, Gorup, Alexander M., MD, and Keen, Monte S., MD, "The Role of Botulinum Toxin A in the Long-term Prevention of Facial Wrinkles: A Preliminary Observational Report", Otolaryngology—Head and Neck Surgery, Aug. 1997, p. 161, vol. 117, No. 2.
Schantz, Edward J., et al., Properties and Use of Botulinum Toxin and Other Microbial Neurotoxins in Medicine, Microbiological Reviews, vol. 56, No. 1, pp. 80-99, Mar. 1992.
Barbier, et al, "Canotoxins Targeting Voltage-Sensitive Na+ Channels", Research Signpost 37/661 (2), Fort P.O., Trivandrum-695 023, Kerala, India, 2003.
Ates, et al, Article Department of Neurosurgery, School of Medicine, Neurol Res Apr. 2007, 29(3) 317-23.
Malhotra, et al, "Specific Toxicity of Paralytic Shellfish Poisons", Article Agricultural Research Laboratory, Dow Chemical U.S.A., 1981.
Letienne, et al, "Pharmacological Characterization of Sodium Channels in Sinoatrial Node Pacemaking in the Rat Heart", Jan. 20, 2006 530(3): 243-9 Epub Dec. 20, 2005.
Llewellyn, Lyndon E., "Saxitoxin, A Toxic marine Natural Product That Targets a Multitude of Receptors", Cambridge, UK, Jan. 25, 2006.
Oshima, Y., Post-Column Derivatization HPLC Method for Paralytic Shellfish Poisons, IOC Manuals and Guides No. 33, pp. 84-91, 1995.
Penzotti, et al, Specific Neosaxitoxin Interactions with the Na+ Channel Outer Vestibule Determined by Mutuant Cycle Analysis, Biophysical Journal, vol. 80, Feb. 2001, pp. 698-706.

* cited by examiner

TRANSDERMAL ADMINISTRATION OF PHYCOTOXINS

FIELD OF THE INVENTION

This invention relates to the transdermal administration of pharmaceutical compositions containing phycotoxins and uses thereof for blocking neuronal transmission. More specifically, the invention relates to methods for the transdermal delivery of heterocyclic guanidine-type compounds for blocking neuronal transmissions and to compositions and products for facilitating transdermal delivery.

BACKGROUND OF THE INVENTION

Paralytic shellfish poisoning (PSP) results from a mixture of phycotoxins that bind reversibly to a receptor site on the voltage-gated sodium channel found in excitable cells. The primary clinical symptom is an acute paralytic illness. Phycotoxins or algal toxins are produced by microscopic planktonic algae. These toxins accumulate on filter feeders such as bivalves. Consumption of phycotoxin-contaminated shellfish results in six diseases in humans: PSP, Diarrhetic shellfish poisoning (DSP), amnesic shellfish poisoning (ASP), neurotoxic shellfish poisoning (NSP), ciguatera poisoning (CP) and cyanobacterial poisoning (CNP).

The phycotoxins that produce PSP have a common structure of 3,4,6-trialquil tetrahidropurine. Twenty-six naturally occurring phycotoxins have been described. These phycotoxins are non-protein, low molecular weight compounds of between 289 and 450 daltons. The gonyautoxins (GTX's) are the most abundant of these phycotoxins found in shellfish extract occurring over 80% of the total toxin content.

The high toxicity of these phycotoxins is due to reversible binding to a receptor site on the voltage-gated sodium channel on excitable cells, thus blocking the influx of sodium ions and preventing nerve and muscle cells from producing action potentials, thereby blocking neuronal transmission and causing death in mammals via respiratory arrest and cardiovascular shock. Application of small amounts of these phycotoxins can produce a flaccid paralysis of striated muscle for periods that are dose dependent.

The presence of wrinkles in the neck and face of people are seen as negative aesthetic effects by social groups. These marks reflect facial aging and increase the subjective awareness of the age of people. Since the beginning of civilization, natural or synthetic chemical compounds have been used and procedures have been developed (i.e. plastic surgery) to alleviate this problem. For example, plastic surgeons and cosmetic centers have been experimenting with, and using, Botulin A toxin as a pharmaceutical preparation that produces facial rejuvenation by removing face wrinkles. Botulin A toxin is a neurotoxin that acts by chemodenervation, or blocking the presynaptic release of the neurotransmitter acetylcholine in the neuromuscular plate, thus interfering with neuromuscular transmission, paralyzing the muscle and preventing its contraction for a period of up to 4 months. Applied locally in the face of people, its effect is a facial rejuvenation that appears within 5-7 days after the toxin is applied. The facial rejuvenation from a dose of Botulin A toxin typically has a duration of approximately 4 months. Botulin A toxin has been used for the treatment of diseases associated with muscular spasm, focal dystonia, sphincter relaxation (achalasia and anal fissure), hyperhydrosis and urinary bladder relaxation.

While Botulin A toxin is effective as a facial rejuvenate, it is an enzyme that is inherently unstable. This instability makes its use and handling problematic. In fact, it requires freezing before use, and it must be used within four hours of opening the container. Because it is an enzyme, Botulin A toxin also generates antibodies that prevent its use in consecutive injections and it can induce an allergic response. In addition, its results are delayed 5-7 days, which is undesirable for patients wanting an immediate result. Another problem with Botulin A toxin is that it leaves a marbled look when used as a facial rejuvenate. Accordingly, a need exists for a facial rejuvenate that is stable, fast-acting, provides a more natural look, and which is not an enzyme.

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum (the outer layer of the epidermis), which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

In order to increase the rate at which a drug penetrates through the skin, then, various approaches have been followed, many of which involve the use of either a chemical penetration enhancer or a physical penetration enhancer. Physical enhancement of skin permeation includes, for example, electrophoretic techniques such as iontophoresis. The use of ultrasound (or "phonophoresis") as a physical penetration enhancer has also been researched. Chemical penetration enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Nevertheless, the number of drugs that can be safely and effectively administered through the skin, without concomitant problems such as irritation and sensitization, remains limited.

There are a number of approaches to the delivery of drugs and other compounds transdermally. For example, in U.S. Pat. No. 4,818,541, transdermal systems are disclosed for delivering phenylpropanolamine to the skin. In the aforementioned patent, however, it is noted that the skin flux of (±)-phenylpropanolamine (i.e., a mixture of (−)-norephedrine and (+)-norephedrine) is only 16 microg/$cm^2$/hr, although the skin flux of individual enantiomers was found to be higher. Furthermore, the method of the '541 patent requires neutralization of phenylpropanolamine hydrochloride (i.e., conversion to the free base), the commercially available form of the drug, before incorporation into a transdermal drug delivery system.

Similarly, U.S. Pat. No. 6,299,902 describes an improved transdermal absorption and efficacy for a local anesthetic. The transdermal preparation contains at least one local anesthetic agent and at least two melting point depressing agents. Also described is a two-phase liquid composition that contains aqueous and oil phases, the oil phase having a relatively high concentration of a local anesthetic agent to enhance transdermal absorption and efficacy when incorporated into an anesthetic preparation. A preferred anesthetic preparation includes lidocaine or tetracaine, thymol or menthol, and ethyl alcohol or isopropyl alcohol.

Although many chemical permeation enhancers are known, there is an ongoing need for specific transdermal pharmaceutical formulations which include chemical permeation enhancers that are highly effective in increasing the rate at which a drug permeates the skin, and do not result in skin damage, irritation, sensitization, or the like.

SUMMARY OF THE INVENTION

In accordance with the objects of the invention, novel compositions and methods for transdermal delivery are provided.

In one aspect of the invention, effective amounts of the pharmaceutical compositions and a transdermal delivery system are provided for transdermal administration of at least one phycotoxin. The pharmaceutical composition contains at least one phycotoxin, and may optionally be specially formulated for transdermal drug delivery. The transdermal drug delivery system may be selected from chemical systems, such as permeation enhancers, and physical means, such as iontophoresis, phonoporesis, sono-macroporation, thermal modulation, magnetic modulation and mechanical modulation.

In yet another aspect of the invention, methods of interfering with neuronal transmission comprising transdermal administration of an effective amount of the pharmaceutical compositions of the invention are provided.

In another aspect of the invention, preparations for facial rejuvenation are provided that comprise an effective amount of the composition of the invention and a facial cream.

DETAILED DESCRIPTION OF THE INVENTION

In accordance with the present invention, it has been found that compositions comprising certain phycotoxins, can be used for many cosmetic or clinical applications, without surgery, and with advantages over alternative compositions, such as Botulin A toxin in the areas of at least: side effects, allergies, immune rejection or hematoma and the time period for the treatment to take effect. The compositions and methods of the present invention may be used to deliver the phycotoxin to a subdermal structure such as a subdermal muscle, a subdermal sweat gland or a subdermal sensory neuron. In accordance with the present invention, muscular relaxation may occur in less than five minutes from the time of penetration of the active ingredient through the skin.

It must be noted that, as used in this specification and the appended claims, the singular forms "a," "an" and "the" include plural referents unless the context clearly dictates otherwise. Thus, for example, reference to "a pharmacologically active agent" includes a mixture of two or more active agents, reference to "an enhancer" includes mixtures of two or more enhancers, and the like.

In describing and claiming the present invention, the following terminology will be used in accordance with the definitions set out below.

As used herein, "an effective amount" is that amount sufficient to interfere with neuronal transmission by blocking the presynaptic release of at least some of the neurotransmitter acetylcholine in the neuromuscular plate, thus interfering with transmission, paralyzing the muscle and preventing it from contracting, or producing a relaxation of contracted muscles.

Amounts are given in units of activity. One unit of activity corresponds to an amount of the composition of the invention necessary to block the muscular contractions of the crural biceps of a 20 gram CF1 albino or a BALB-C strain mouse leg for 1.5 to 2.0 hours. The toxin is intramuscularly injected in the crural biceps of the mouse right leg in a volume of 0.5 ml. The left leg is used as a control.

In order to measure the amount of toxin used in each dose, High Performance Liquid Chromotography (HPLC) analysis can be performed with on line fluorescence detection (HPLC-FLD). This method allows the measurement of the mass of each toxin in any mixture, extract or pharmaceutical formulation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of one or more symptoms or underlying causes in a predisposed individual, as well as treatment of one or more symptoms or underlying causes in a clinically symptomatic individual.

The terms "active," "active agent," "drug" and "pharmacologically active agent" are used interchangeably herein to refer to a chemical material or compound that induces a desired effect, and include agents that are therapeutically effective, prophylactically effective, or cosmetically effective. Also included are derivatives, metabolites and analogs of those compounds or classes of compounds specifically mentioned which also induce the desired effect.

"By therapeutically effective" amount is meant a nontoxic but sufficient amount of an active agent to provide the desired therapeutic effect.

By "transdermal" drug delivery or "topical administration" is meant administration of a drug to the skin surface of an individual so that the drug passes through the skin tissue. The terms "transdermal" and "topical" are intended to include "transmucosal" drug administration, i.e., administration of a drug to the mucosal (e.g., sublingual, buccal, vaginal, rectal) surface of an individual so that the drug passes through the mucosal tissue. Transdermal delivery or topical administration may result in delivery into, for example, the individual's blood stream, thereby producing a systemic effect, or may result in delivery to, for example, a muscle or neuron, thereby providing a localized effect. Unless otherwise stated or implied, the terms "topical drug administration" and "transdermal drug administration" are used interchangeably.

The term "body surface" is used to refer to skin or mucosal tissue.

"Predetermined area" of skin or mucosal tissue, refers to an area of skin or mucosal tissue through which an active agent is delivered, and is intended to define an area of intact unbroken living skin or mucosal tissue. That area will usually be in the range of about 5 $cm^2$ to about 200 $cm^2$, more usually in the range of about 5 $cm^2$ to about 100 $cm^2$, preferably in the range of about 20 $cm^2$ to about 60 $cm^2$. However, it will be appreciated by those skilled in the art of drug delivery that the area of skin or mucosal tissue through which the drug is administered may vary significantly, depending on factors such as the desired treatment, whether a delivery device is employed, dose, the size of the treatment area, and other factors.

"Penetration enhancement" or "permeation enhancement" as used herein refers to an increase in the rate at which the active agent permeates through the skin or mucosal membrane, relative to penetration of the same active agent when applied alone (i.e., the "flux" of the agent through the body surface). The enhanced permeation effected through the use of such enhancers can be observed by measuring the rate of diffusion of drug through animal or human skin using, for example, a Franz diffusion apparatus as known in the art.

An "effective amount of a permeation enhancer" refers to a non-toxic amount or quantity of the enhancer or penetration-enhancing treatment, which is sufficient to provide the desired increase in penetration rate. Permeation enhancers may also influence the depth of penetration, rate of administration, and amount of drug delivered.

"Carriers" or "vehicles" as used herein refer to carrier materials suitable for transdermal or topical drug administration. Carriers and vehicles useful herein include any such materials known in the art which is non-toxic in the amounts used, and does not interact with other components of the composition in a deleterious manner.

The compositions of the invention comprise an effective amount of at least one phycotoxin. More preferably, the compositions of the invention comprise an effective amount of at least one compound represented by formula I set forth below:

Formula I

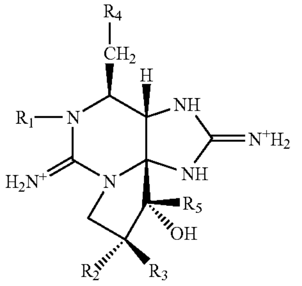

wherein $R_1$ and $R_5$ are independently selected from the group consisting of —H and —OH; $R_2$ and $R_3$ are independently selected from the group consisting of —H and —$SO_3$; and $R_4$ is selected from the group consisting of —H, —OH, —$COONH_2$, —$COONHSO^-_3$ and —$COOCH_3$, and a pharmacologically acceptable carrier.

Preferred tricyclic 3,4-propinoperhydropurines in accordance with the present invention are the saxitoxins and the gonyautoxins (hereinafter "GTX") of the formula I as set forth in the table below.

| Compound | $R_1$ | $R_2$ | $R_3$ | $R_4$ | $R_5$ |
|---|---|---|---|---|---|
| Gonyautoxin 1 | —OH | —H | —$OSO^-_3$ | —$COONH_2$ | —OH |
| Gonyautoxin 2 | —H | —H | —$OSO^-_3$ | —$COONH_2$ | —OH |
| Gonyautoxin 3 | —H | —$OSO^-_3$ | —H | —$COONH_2$ | —OH |
| Gonyautoxin 4 | —OH | —$OSO^-_3$ | —H | —$COONH_2$ | —OH |
| Gonyautoxin 5 | —H | —H | —H | —$COONHSO^-_3$ | —OH |
| Saxitoxin | —H | —H | —H | —$COONH_2$ | —OH |
| Neosaxitoxin | —OH | —H | —H | —$COONH_2$ | —OH |
| Descarbamoylsaxitoxin | —OH | —H | —H | —OH | —OH |

In one aspect of the invention, the pharmaceutical compositions of the invention comprise at least one phycotoxin. In a more preferred embodiment, compositions of the present invention include at least one GTX compound selected from GTX 1, GTX 2, GTX 3, GTX 4 and GTX 5. In other aspects of the invention, the pharmaceutical compositions comprise a mixture of two or more phycotoxins. For example, mixtures of two or more GTX compounds are contemplated. Alternatively, the pharmaceutical compositions of the invention comprise at least one compound selected from the group consisting of saxitoxin (STX), neosaxitoxin, and decarbamoylsaxitoxin, either alone, or in combination with one or more of GTX's 1-5, Botulin A toxin and tetrodotoxin. It should be understood by those of skill in the art that, subject to the conditions set forth with respect to the formula I above, other mixtures and combinations of tricyclic 3,4-propinoperhydropurines are within the scope of this invention. Particularly preferred compositions include a mixture of GTX 2 and GTX 3 and, optionally, contain one or both of GTX 1 and GTX 5. In mixtures of GTX 2 and GTX 3, a weight ratio of GTX 2/GTX 3 of about 2:1 is preferred.

In one embodiment of the invention, one or more compounds of the formula I are used in combination with an effective amount of Botulin A toxin. In this embodiment, the pharmaceutical compositions of the invention comprise an effective amount of Botulin A toxin and an effective amount of at least one tricyclic 3,4-propinoperhydropurine of the formula I. The combination may be used in any cosmetic or clinical application in which the compounds of the invention, or Botulin A toxin are used.

The present invention includes the use of toxins obtained or processed by bacterial culturing, toxin extraction, concentration, preservation, freeze drying, and/or reconstitution, as well as modified or recombinant toxins, and derivatives or fragments of toxins made by recombination.

Generally, the pharmaceutical compositions of the invention are applied locally in the form of a preparation for application to the skin. To form such a preparation, an effective amount of the phycotoxin of the invention is added to a pharmacologically acceptable carrier. As compared to Botulin A toxin, preparations which employ a compound of the formula I are typically more stable than. Botulin A toxin at room temperature, generally do not require refrigeration, generally are sterilizable, are expected to be substantially non-allergenic since they are not peptide-based, usually act substantially immediately, and, in many cases, may be applied repeatedly without significant, adverse side effects.

Without being bound by theory, when applied locally, these compounds appear to carry out their antispasmodic action by blocking the spreading of nervous impulse, or neuronal transmission, by reversibly binding to the sole biological molecular receptor, i.e. the voltage gated sodium channel, present in all neurons and excitable cells. By binding to this channel, there is no entry of sodium to the neuronal cell; depolarization does not occur and, therefore, propagation of the impulse is stopped. This action mechanism blocks the presynaptic release of the neurotransmitter acetylcholine in the neuromuscular plate, thus interfering with neuromuscular transmission, paralyzing the muscle and preventing it from contracting, or producing a relaxation of muscles contracted by pathological problems. This mechanism is particularly efficient for cosmetic purposes, as it can be used to selectively interfere with certain facial muscles, namely, those associated with and responsible for the formation of wrinkles, thus producing the sought-after effect of facial rejuvenation.

The pharmaceutical preparations of the invention are applied locally in the vicinity of the muscle that is to be paralyzed or prevented from contracting. The transdermal application should be in amounts sufficient to provide from 1-1000 units of activity to the muscle. The effect is immediately apparent, generally occurring within a maximum of 30 seconds to five minutes after penetration of the active compound through the skin. The maximum effect is generally achieved within 15 minutes of penetration of the active compound through the skin. Its effective duration depends on the dose administered, the muscle in question, as well as the volume and specific composition administered. This is the pattern for all clinical applications and pathologies.

The compositions and methods of the present invention can be used for, for example, neuromuscular disorders associated with spastic muscles, sympathetic neuronal disorders such as hyperactive sweat glands, to reduce inflammation or pain due to inflammation, to treat blepharospasm, strabismus, focal dystonia, sphincter relaxation (achalasia and anal fissure), hyperhydrosis, urologic disorders by, for example, urinary bladder relaxation, muscular spasm-related pain management, muscular spasms, wound treatment, facial wrinkle removal, carpal-tunnel syndrome, fibromyalgia, joint flare, post-operative pain management, arthritis, sciatica, tendonitis, neck pain or neck injury, back pain, hemifacial spasm, hyperfunctional larynx, juvenile cerebral palsy, spasticity, headaches including migraine headaches, writer's cramp, miofacial pain, tremors, tics, bruxism, temporomandibular joint disorders, cervical dystonia, oramandibular dystonia, dental anesthesia, treatment of dental pain, hair growth, gastrointestinal disorders, hyperfunctional facial lines, cosmetic disorders, shoulder pain, rotator cuff injuries, peripheral nerve dysfunction, migraine or tension headaches, strokes, problems with motor control such as Parkinson's disease, management of painful injections including Restalyn™ shots, allergy shots and I.V. placement.

This invention is not limited to specific drug delivery systems, device structures, enhancers or carriers, as such may vary. It is also to be understood that the terminology used herein is for the purpose of describing particular embodiments only, and is not intended to be limiting.

In a first aspect, the present invention relates to a composition for application to the skin. The composition of the present invention may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see Remington: The Science and Practice of Pharmacy for further information.

Creams, are also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol.RTM. trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, as is known in the art, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Liposome preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin™ (GEBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the compositions of the present invention. For example, solvents, including alcohol, may be used to facilitate solubilization of the active agent. Other optional additives include opacifiers, antioxidants, fragrance, colorant, gelling agents, thickening agents, stabilizers, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The concentration of the active agent in the formulation can vary a great deal, and will depend on a variety of factors, including the condition to be treated, the desired effect, the ability and speed of the active agent to reach its intended target, and other factors within the particular knowledge of the patient and physician. Preferred formulations will typically contain a sufficient amount of the active agent to deliver a dose on the order of about 1-5000 units of the active agent to the treatment site. More preferably, the delivered dose is about 20-1000 units of activity. Even more preferably, the delivered dose is more than 32 units of activity up to 5000 units of activity, or more than 32 units of activity up to 1000 units of activity, and most preferably, the delivered dose is more than 40 units of activity up to 1000 units of activity, even more preferably, the delivered dose is about 50-400 units of activity, or 75-200 units of activity.

In another aspect, the invention pertains to a method, composition and drug delivery system for increasing the rate at which the active agent, permeates through the body surface of a patient, and/or the amount of material that permeates through the body surface of a patient. The method involves administering the agent to a predetermined area of the patient's body surface in combination with a permeation enhancer and/or a permeation enhancing treatment.

One class of suitable permeation enhancers are chemical permeation enhancers, such as a hydroxide-releasing agent in an amount effective to enhance the flux of the agent through the body surface without causing damage thereto, or in combination with an ultrasound treatment. Other suitable chemical permeation enhancers are described in, for example, W. R. Pfister and D. S. T. Hsieh, "Permeation Enhancers Compatible with Transdermal Drug Delivery Systems, Part I: Selection and Formulation Considerations," *Pharm. Technol.*, September 1990, and W. R. Pfister and D. S. T. Hsieh, "Permeation Enhancers Compatible with Transdermal Drug Delivery Systems, Part II: System Design Considerations," *Pharm. Technol.*, October 1990, the disclosures of which are hereby incorporated by reference to describe suitable chemical permeation enhancers. Exemplary chemical permeation enhancers for use in the present invention include, but are not limited to, alcohols, amines and amides, such as urea, amino acids, amino acid esters, Azone®, pyrrolidones, terpenes, fatty acids, fatty acid esters, macrocyclic compounds, tensides, sulfoxides, liposomes, transferomes, lecithin vesicles, ethosomes, water, anionic, cationic and non-ionic surfactants, polyols and essential oils.

Specific compounds that may be used to enhance skin permeability include: the sulfoxides dimethylsulfoxide (DMSO) and decylmethylsulfoxide ($C_{10}$ MSO); ethers such as diethylene glycol monoethyl ether (available commercially as Transcutol™) and diethylene glycol monomethyl ether; surfactants such as sodium laurate, sodium lauryl sulfate, cetyltrimethylammonium bromide, benzalkonium chloride, Poloxamer™ (231, 182, 184), Tween™ (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone™ from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, sorbitan sesquioleate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanol amine, diethanol amine and trethanolamine; alkanones, and organic acids, particularly salicylic acid and salicylates, citric acid and succinic acid. Percutaneous Penetration Enhancers, eds. Smith et al. (CRC Press, 1995) provides an excellent overview of the field and further background information on a number of chemical and physical enhancers.

The GTX compounds of the present invention are typically small molecules having relatively low molecular weights, are water-soluble and have a positive charge associated with the compounds and thus are cationic. Ideally, transdermal penetration is carried out using small molecules that are fat-soluble and have a neutral charge.

Thus, in the present case, it may be desirable, under certain circumstances, to employ anionic chemical permeation enhancers and/or anionic surfactants to improve the transdermal delivery of the GTX compounds. Also, since fat solubility may improve transdermal delivery, it may be desirable to chemically modify the GTX compounds to change their hydrophilic-lipophilic balance (HLB) and render them more fat-soluble. One example of such a modification might be to add a lipophilic "tail" to the GTX molecule by, for example, attaching a long chain fatty molecule to the GTX molecule in any suitable, conventional manner.

The phycotoxins employed in the present invention are non-protein, low molecular weight compounds of between 289 and 450 daltons. This provides several advantages over prior art compositions used for similar purposes. First, since the phycotoxins are non-protein, the likelihood of allergic reactions to the phycotoxins is very low. Second, the small size of the phycotoxins makes them excellent candidates for transdermal delivery. Also, the phyxotoxins of the present invention are very potent, relative to Botulin A toxin, and thus smaller amounts can be used to achieve longer lasting effects. In addition, the phycotoxins of the present invention often exhibit a shorter time period until the effect is realized, in comparison to Botulin A toxin. Also, the small size of the phycotoxins allows them to be passed out of the body relatively quickly, thereby reducing the risk of harmful side effects or toxin buildup in the body.

Thus, the present method of transdermally delivering the active agent may vary, but necessarily involves application of a composition containing a tricyclic 3,4-propinoperhydropurine to a predetermined area of the skin or mucosal tissue for a period of time sufficient to provide an effective blood level or penetration level of drug. The method may involve direct application of the composition as an ointment, gel, cream, or the like, or may involve use of a drug delivery device as taught in the art, e.g., in U.S. Pat. Nos. 4,915,950, 4,906,463, 5,091,186 or 5,246,705, the disclosures of which are hereby incorporated by reference for the purpose of describing specific transdermal drug delivery devices, or as described below.

Transdermal Delivery Systems

An alternative and preferred method for administering a tricyclic 3,4-propinoperhydropurine transdermally involves the use of a drug delivery system, e.g., a topical or transdermal "patch," wherein the active agent is contained within a laminated structure that is to be affixed to the skin. In such a structure, the active agent is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility an, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or is may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of the drug to be delivered and the flux of the drug through the body surface. Larger patches will be necessary to accommodate larger quantities of drug, while smaller patches can be used for small quantities of drug and/or drugs that exhibit a relatively high permeation rate.

Such drug delivery systems may be fabricated using conventional coating and laminating techniques known in the art. For example adhesive matrix systems can be prepared by casting a fluid admixture adhesive, drug and vehicle onto the backing layer followed by lamination of the release liner. Similarly the adhesive mixture may be cast onto the release liner, followed by lamination of the release liner. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device. For active agents that are obtained in salt form, an enhancer that doubles as a neutralizing agent is incorporated into the device during patch manufacture rather than subsequent to preparation of the device. Thus, for acid addition salts of tricyclic 3,4-propinoperhydropurine, e.g., the hydrochloride salt of tricyclic 3,4-propinoperhydropurine, a basic enhancer such as a hydroxide-releasing agent will neutralize the drug during manufacture of the transdermal system, resulting in a final drug delivery device in which the drug is present in nonionized, neutral form, preferably along with an excess of the basic compound to serve as a permeation enhancer.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such an adhesive overlayer, the delivery system remains in place for the required period of time.

Other types and configurations of transdermal drug delivery systems may also be used in conjunction with the method of the present invention, i.e., the use of a hydroxide-releasing agent as a permeation enhancer, as will be appreciated by those skilled in the art of transdermal drug delivery. See, for example, Ghosh, Transdermal and Topical Drug Delivery Systems (Interpharm Press, 1997), particularly Chapters 2 and 8. In addition, two or more transdermal delivery systems may be combined.

A variation of the transdermal patch that can be used in accordance with the present invention is the use of transdermal delivery devices that deliver a low-level electrical energy to actively transport the active agents through intact skin. In this case, a drug reservoir is attached to the patient, in much the same manner as the transdermal patch described above. The device further includes electrodes and a power source for providing low-level electrical energy. This device can also be employed in conjunction with the various optional features of the transdermal patch delivery system described above.

The use of electrical energy for transdermal delivery provides the additional advantage that the device can be used to allow on-demand dosing of the material by providing the patient with a button or other activating device for activating the delivery of electrical energy. In addition, the device may be provided with a controller that can perform several functions. For example, the controller may be used to limit the amounts and time periods wherein a patient may exercise control of on-demand dosing. Alternatively, the controller can control all dosing functions and no on-demand feature need be provided. In a further alternative the controller may be combined with the on-demand feature to provide a certain level of minimum dosing, but allow the patient to increase the dosage, on-demand, if desired. Again, the controller may be programmed to prevent the patient from exceeding a maximum, safe dosage over a pre-determined time period. A suitable example of such a transdermal delivery system is the E-TRANS® transdermal technology of Alza.

Another transdermal drug delivery system that may be used in the present invention is a crystal reservoir patch (available from, for example, Avena Drug Delivery Systems) wherein at least a portion of the medicament is present in the form of crystals that can be solubilized over time to provide a continuing supply of the medicament from the patch. The crystal reservoir system allows for a smaller transdermal patch due to an oversaturation of the adhesive polymer with medicament to the point that the medicament forms crystals. A higher concentration of medicament due to the presence of both solid crystals and solute also yields a more consistent supply of medicament within the patch. The medicament equilibrium shifts as medicament is absorbed through the skin forcing the dissolution of the crystals into the solute thus maintaining the maximum presentation of medicament at the contact site as well as allowing for a more even absorption of medicament.

In another embodiment of the present invention, a physical transdermal permeation enhancement method selected from iontophoresis, phonophoresis, sono-macroporation, thermal modulation, magnetic modulation, and mechanical modulation, may be employed either alone, or in combination with another physical or chemical permeation enhancer. Examples of most of these methods can be found in, for example, "Drug Permeation Enhancement, Theory and Applications," D. S. T. Hsieh, ed., Marcel Dekker, New York, N.Y. (1994).

Iontophoresis can deliver the toxin to a subdermal site by passing electrical current across a patch or skin area containing a composition comprising the toxin. In certain embodiments, an electrode may be place on the external surface of a transdermal patch or on the skin, and a ground electrode is placed elsewhere. Current is applied to cause the toxin to penetrate the skin. The amount of current is typically less than 1 $mA/cm^2$ and preferably 0.3 to 0.7 $mA/cm^2$ are employed. Since the various GTX's have a +1 charge, this facilitates penetration into the skin both, in comparison to other molecules having a +2 charge, for example, but also via the application of intophoresis.

Particularly preferred methods of permeation enhancement are phonoporesis and sono-macroporation. These methods offer several advantages including bypassing the gastrointestinal degradation and hepatic first-pass metabolism encountered in oral administration of medicaments, improves patient compliance since it is non-invasive, may eliminate the need to use chemical permeation enhances which can damage the skin, can be used to deliver the active ingredients in ionic or non-ionic form, works well with both aqueous and non-aqueous carriers, can deliver the actives to deep subcutaneous tissues, and these methods can be used in combination with other transdermal delivery systems such as transdermal patches, and/or permeation enhancers. Phonoporesis has been used to deliver local anesthetics in, for example, E. J. Novak, *Arch. Phys. Med. Rehabil*, May, 231 (1964), and H. A. E. Benson, J. C. MeElnay, and R. Harland, *Int. J. Pharm.*, 44, 65 (1988). Suitable conditions for phonoporesis are described in, Y. Sun and J. C. Liu, "Transdermal Drug Delivery by Phonoporesis: Basics, Mechanisms, and Techniques of Application," Chapter 15, "Drug Permeation Enhancement Theory and Applications," D. S. T. Hsieh, Ed., Marcel Dekker, New York, N.Y. (1994), the disclosure of which is hereby incorporated by reference for the purpose of describing suitable phonoporesis conditions.

If phonoporesis is to be employed, the composition should contain a suitable coupling agent for transfer of acoustic energy from the surface of the transducer to a patient. Water is a preferred coupling agent since there is only a small difference between the acoustic impedance of water and that of soft tissue. Alternatively, commercially available coupling agents, such as aqueous thixotropic gels, glycerol, and mineral oil, may be employed.

In carrying out phonoporesis, frequencies of from about 10 kHz to about 20 MHz may be employed. More preferably, frequencies of from about 1 MHz to about 16 MHz are used. The ultrasound may be continuous or pulsed and the intensity and duration of the treatment can be determined by a person skilled in the art depending on the patient and the desired level of drug delivery required. Typically, intensities of less than about 2 $W/cm^2$ are applied in phonoporesis.

Alternatively, sono-macroporation may be employed. If sono-macroporation is employed, typically acoustic intensities of more than 2 $W/cm^2$ up to about 40 $W/cm^2$ will be employed in combination with frequencies of about 10-100 kHz, more preferably, 20-80 kHz. Sono-macroporation is most useful for enhancing the permeation of larger molecules having molecular weights of about 400-600 kDa.

As with the formulations of the invention discussed in the preceding section, the composition containing the tricyclic 3,4-propinoperhydropurine within the drug reservoir(s) of the laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Utility and Administration

The formulations and delivery systems of the invention are useful for transdermal administration of a phycotoxin such as tricyclic 3,4-propinoperhydropurine to treat any condition, disease or disorder that is responsive to administration of a tricyclic 3,4-propinoperhydropurine. Typically, the formulations and delivery systems of the invention are used to administer a tricyclic 3,4-propinoperhydropurine as an anesthetic agent (i.e., for pain relief) or to decrease muscle contractions. Most commonly, the compounds are used as a local anesthetic or a muscle relaxant.

The periodic dosage administered will, of course, vary from subject to subject and depend on the particular disorder or condition, the severity of the symptoms, the subject's age, weight and general condition, and the judgment of the prescribing physician. Other factors specific to transdermal drug delivery include the solubility and permeability of the carrier and adhesive layer in a drug delivery system, if one is used, and the period of time for which such a device will be affixed to the skin or other body surface. Generally, however, a periodic dosage using the present formulations and delivery systems will be an amount sufficient to deliver 1-1000 units of activity of the tricyclic 3,4-propinoperhydropurine to the treatment area, per dose. Dosing can be repeated at any interval, depending primarily on factors such as the initial dosage administered, the desired duration of the treatment, the condition or disorder being treated, the type of active agent employed, etc. Skilled persons will be able to determine the proper periodic dosages for a given condition, disorder or treatment, talking into account these and other relevant factors.

The invention accordingly provides a novel and highly effective means for administering a tricyclic 3,4-propinoperhydropurine through the body surface (skin or mucosal tissue) of a human or animal. Advantages of the present invention, relative to use of Botulin A toxin, may be realized in the higher efficacy and thus lower dosage of the compositions of the present invention, relative to Botulin A toxin, the relatively immediate onset of activity that is achieved by the present invention, and the fact that the present compositions are more storage stable and thus more suitable than Botulin A toxins for topical formulations. Also, it is believed that the compositions of the present invention will provide a more natural look than that which is achieved with Botulin A toxin, when used, for example, as a facial rejuvenate. The invention thus represents an important advance in the field of transdermal drug delivery.

The practice of the present invention will employ, unless otherwise indicated, conventional techniques of drug formulation, particularly topical drug formulation, which are within the skill of the art. Such techniques are fully explained in the literature. See Remington: The Science and Practice of Pharmacy, cited supra, as well as Goodman & Gilman's The Pharmacological Basis of Therapeutics, 9th Ed. (New York: McGraw-Hill, 1996).

EXAMPLE 1

Cosmetic Gel for Treatment of Wrinkles

| | |
|---|---|
| Ethoxydiglycol | 6.500% w/w |
| Laureth-7 | 1.000% w/w |
| Diazolidinyl urea | 0.300% w/w |
| Methylparaben | 0.150% w/w |
| Propylparaben | 0.050% w/w |
| Hydroxyethyl cellulose | 1.500% w/w |
| Toxins GTX2/GTX3 | 0.01-0.0001% w/w |
| Water to | 100% w/w |

Purpose of ingredients:
Ethoxydiglycol: Penetration-enhancer (organic solvent)
Laureth-7: Penetration enhancer (surfactant)
Diazolidinyl urea, Methylparaben, Propylparaben: Preservatives
Hydroxyethyl cellulose: Thickener
Compounding Procedure:

Dissolve all ingredients, except for hydroxyethyl cellulose, in water and mix to make a clear, uniform solution. Disperse the hydroxyethyl cellulose polymer with vortex mixing and continue mixing without vortex until a smooth, clear gel forms.

EXAMPLES 2-4

Creams for Topical Administration

| Cream N° 1 | |
|---|---|
| Ingredient | % w/w |
| Water to | 100.00 |
| Propylene glycol | 5.00 |
| Glyceryl monostearate | 4.50 |
| Squalene | 4.50 |
| Propylene glycol dicaprylate/caprate | 4.00 |
| Cyclomethicone | 3.00 |
| Cetyl lactate | 2.50 |
| DMDM hydantoin (and) Iodo propynyl butyl carbamate | 0.15 |
| Glyceryl stearate/PEG 100 stearate | 0.80 |
| PVM/MA decadiene crosspolymer | 0.25 |
| Triethanolamine | 0.16 |
| Alpha tocopherol (and) ascorbyl palmitate (and) lecithin (and) glyceryl stearate (and) glyceryl oleate (and) citric acid | 0.05 |
| EDTA disodium | 0.02 |
| Toxins GTX2/GTX3 | 0.01-0.0001 |

| Cream N° 2 | |
|---|---|
| Ingredients | % w/w |
| Water to | 100.00 |
| Polyglyceryl methacrylate | 5.00 |
| Hydrogenated polyisobutene | 5.00 |
| Propylenglycol | 5.00 |
| Propylenglycol dicaprylate/caprate | 4.00 |
| Cetylic alcohol | 3.00 |
| Cyclomethicone | 2.00 |
| Diazolidinyl urea (and) methylparaben (and) propylparaben (and) propylene glycol | 1.00 |
| Cetearylic alcohol (and) ceteareth 20 | 0.70 |

-continued

| Cream N° 2 | |
|---|---|
| Ingredients | % w/w |
| Methyl glucose dioleate | 0.50 |
| Triethanolamine | 0.28 |
| Alpha tocopherol (and) ascorbyl palmitate (and) lecithin (and) glyceryl stearate (and) glyceryl oleate (and) citric acid | 0.05 |
| EDTA disodium | 0.02 |
| Toxins GTX2/GTX3 | 0.01-0.0001 |

| Cream N° 3 | |
|---|---|
| Ingredients | % w/w |
| Water to | 100.00 |
| Glyceryl distearate (and) PEG-150 stearate (and) glyceryl stearate (and) cetearylic alcohol (and) cetylic alcohol (and) stearic acid | 5.30 |
| Glycerine | 2.00 |
| Dicaprylyl carbonate | 2.00 |
| Diazolydinyl urea (and) Iodo propynyl butyl carbamate | 1.00 |
| Dimethicone | 0.50 |
| Sodium polyacrylate | 0.35 |
| Cetylic alcohol | 0.30 |
| Alpha tocopherol (and) ascorbyl palmitate (and) lecithin (and) glyceryl stearate (and) glyceryl oleate (and) citric acid | 0.05 |
| Triethanolamine | 0.05 |
| EDTA disodium | 0.02 |
| Toxins GTX2/GTX3 | 0.01-0.0001 |

EXAMPLE 5

Ointment

| | |
|---|---|
| Petrolatum | 75.000% w/w |
| Sorbitan sesquioleate | 10.000% w/w |
| White Wax | 10.000% w/w |
| Toxins GTX2/GTX3 | 0.01-0.0001% |
| Water to | 100% |

Purpose of Ingredients:
Petrolatum: Emollient ointment base
Sorbitan sesquioleate: Emulsifier, penetration enhance
White Was: Thickener, Stabilizer
Compounding Procedure:

Melt the petrolatum, sorbitan sesquioleate and white wax at 60 degrees C. and mix until uniform. Slowly incorporate the aqueous solution of toxin and continue mixing until the ointment congeals.

EXAMPLE 6

A cream formulation containing a mixture of GTX2/GTX3 was applied to the forehead (glabellar or frown lines) and around the eyes (crow feet wrinkles) of a healthy adult volunteer. After application, the area was treated for 30 seconds with a hand-held sonicator (Beauty Care System, Model JS-2000, Annapolis, Md. USA) to accelerate transdermic absorption. The application of the cream induced reduction of wrinkles that lasted over 24 hours.

EXAMPLE 7

Doses of 200 units up to 5,000 units of a mixture of GTX 2 and GTX 3, as employed in example 2, have been administered by injection in the internal anal sphincter, in normal volunteers. These doses were well tolerated, without adverse or negative side effects. The volunteers remained healthy during and after the local injection of this relatively large amount of toxins.

EXAMPLE 8

One unit of activity corresponds to an amount of the composition of the invention necessary to block the muscular contractions of the crural biceps of a 20 gram CF1 albino strain mouse leg for 1.5 to 2.0 hours. The toxin was intramuscularly injected in the crural biceps of the mouse right leg in a volume of 0.5 ml. The left leg is used as a control. This was done in three mice and the paralyzing effect was tested every 30 minutes for the first two hours, and then every 2, 4, 8 hours and overnight. Depending on the dose injected, the paralyzing effect can last 24 hours or longer. This example confirms the reversible nature of the effect of the toxins of the present invention and demonstrates that the duration of the effect can be controlled by varying the dosage of the toxins.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

What is claimed is:

1. A non-local analgesic method of treating joint pain or neuropathic pain in a patient in need thereof comprising topically administering to said patient a composition comprising a therapeutically effective amount of one or a combination of compounds selected from the group consisting of: GTX-1, GTX-2, GTX-3, GTX-4 and GTX 5.

2. The method of claim 1, wherein the composition comprises GTX-2 and GTX-3.

3. The method of claim 1, wherein the therapeutically effective amount comprises from about 1 to about 5000 units of activity.

4. The method of claim 1, wherein the therapeutically effective amount comprises from about 10 to about 1000 units of activity.

5. The method of claim 1, wherein the therapeutically effective amount comprises from more than 40 to about 1000 units of activity.

6. The method of claim 1, wherein said composition further comprises a penetration enhancer.

7. The method of claim 6, wherein the penetration enhancer is selected from the group consisting of: alcohols, amines, amides, amino acids, amino acid esters, 1-substituted azacycolheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols and essential oils.

8. The method of claim 6, wherein the penetration enhancer is selected from the group consisting of: dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, Poloxamer™231, Poloxamer™182, Poloxamer™184, Tween™20, Tween™40, Tween™60, Tween™80, lecithin, 1-n-dodecylcyclazacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, polyethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

9. The method of claim 6, wherein the penetration enhancer is sorbitan sesquioleate.

10. A method of treating joint pain or neuropathic pain comprising topically administering to a patient a composition comprising a therapeutically effective amount of at least one compound selected from the group consisting of: GTX-1, GTX-2, GTX-3, GTX-4 and GTX-5, and utilizing at least one transdermal delivery step selected from the group consisting of: iontophoresis, phonophoresis, sono-macroporation, thermal modulation, magnetic modulation, and mechanical modulation to enhance the permeation of said topically applied composition into skin of a patient.

11. The method of claim 10, wherein the composition comprises GTX-2 and GTX-3.

12. The method of claim 10, wherein the therapeutically effective amount comprises from about 1 to about 5000 units of activity.

13. The method of claim 10, wherein the therapeutically effective amount comprises from about 10 to about 1000 units of activity.

14. The method of claim 10, wherein the therapeutically effective amount comprises from more than 40 to about 1000 units of activity.

15. The method of claim 10, wherein the transdermal delivery step is iontophoresis.

16. The method of claim 10, wherein the transdermal delivery step is phonophoresis.

17. The method of claim 10, wherein the transdermal delivery step is sono-macroporation.

18. The method of claim 10, wherein the transdermal delivery step is thermal modulation.

19. The method of claim 10, wherein the transdermal delivery step is magnetic modulation.

20. The method of claim 10, wherein the transdermal delivery step is mechanical modulation.

21. The method of claim 10, wherein at least two different transdermal delivery steps are employed.

22. The method of claim 10, wherein said composition further comprises at least one permeation enhancer.

23. The method of claim 10, wherein the topical composition comprises from about 0.0001% to about 0.01% by weight of one or more of said compounds, based on the total weight of the composition.

24. The method of claim 22, wherein the penetration enhancer is selected from the group consisting of: alcohols, amines, amides, amino acids, amino acid esters, 1-substituted azacycloheptan-2-ones, pyrrolidones, terpenes, fatty acids, fatty acid eseters, macrocyclic compounds, tensides, sulfoxides, liposomes, transferomes, lecithin vesicles, ethosomes, anionic, cationic and non-ionic surfactants, polyols and essential oils.

25. The method of claim 22, wherein the penetration enhancer is selected from the group consisting of: dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, Poloxamer™231, Poloxamer™182, Poloxamer™184, Tween™20, Tween™40, Tween™60, Tween™80, lecithin, 1-n-dodecylcyclazacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, polyethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

26. The method of claim 22, wherein the penetration enhancer is sorbitan sesquioleate.

* * * * *